United States Patent [19]

Tietz

[11] Patent Number: 5,053,482
[45] Date of Patent: Oct. 1, 1991

[54] POLYESTERS AND THEIR USE IN COMPOSTABLE PRODUCTS SUCH AS DISPOSABLE DIAPERS

[75] Inventor: Raymond F. Tietz, Wilmington, Del.

[73] Assignee: E. I. Du Pont de Nemours and Company, Wilmington, Del.

[21] Appl. No.: 522,134

[22] Filed: May 11, 1990

[51] Int. Cl.$^5$ .......................................... C08G 63/688
[52] U.S. Cl. ................................ 528/272; 528/275; 528/293; 528/295; 528/300; 528/302; 528/308.6; 264/103; 264/176.1; 525/425; 525/444; 428/480
[58] Field of Search ............... 528/272, 275, 293, 295, 528/300, 302, 308.6; 264/103, 176.1; 525/425, 444; 428/480

[56] References Cited

U.S. PATENT DOCUMENTS

| | | | |
|---|---|---|---|
| 3,018,272 | 1/1962 | Griffing et al. | 528/293 |
| 3,853,820 | 12/1974 | Vachon | 528/295 |
| 4,418,116 | 11/1983 | Scott | 428/288 |
| 4,483,976 | 11/1984 | Yamamoto et al. | 528/295 |
| 4,526,738 | 7/1985 | Miyoshi et al. | 264/176 |
| 4,704,329 | 11/1987 | Hancock et al. | 428/369 |
| 4,883,706 | 11/1989 | Grosjean | 428/215 |

OTHER PUBLICATIONS

Ingamells, J. Appl. Poly. Sci., vol. 26, 4087–4101 (1981).
Grassie, "Developments in Polymer Degradation-5", pp. 112–119, (1984), Applied Science Publishers.

Primary Examiner—John Kight, III
Assistant Examiner—S. A. Acquah

[57] ABSTRACT

The invention provides novel polyesters, fibers and films, nonwovens from the fibers and disposable products of the polyesters such as diapers from the nonwovens. The products are degradable under the conditions typically existing in waste composting processes, have low ingredient costs and yet provide strength and toughness properties adequate for end uses such as in disposable diapers. The polyesters are based upon polyethylene terephthalate copolymerized with diethylene glycol and a 5-sulfoisophthalic acid.

11 Claims, No Drawings

POLYESTERS AND THEIR USE IN COMPOSTABLE PRODUCTS SUCH AS DISPOSABLE DIAPERS

FIELD OF THE INVENTION

This invention relates to novel polyesters and products therefrom. The products include fibers, films, nonwovens from the fibers and disposable products such as diapers from the nonwovens. The products are degradable to innocuous materials under conditions used in municipal solid waste composting systems.

BACKGROUND OF THE INVENTION

The inadequate treatment of municipal solid waste which is being put in landfills and the increasing addition of nondegradable materials, including plastics, to the municipal solid waste streams are combining to reduce drastically the number of landfills available and to increase the costs of municipal solid waste disposal. While the recycling of reusable components of the waste stream is desirable in many instances, there are some products which do not readily fit into this framework, e.g. disposable personal absorbents such as diapers and sanitary napkins, garbage bags, and numerous other products. The composting of non-recyclable solid waste is a recognized and growing method of reducing solid waste volume for landfilling and/or making a useful product from the waste to improve the fertility of fields and gardens. One of the limitations to marketing such compost is the visible contamination by undegraded plastic such as film and fiber fragments.

One object of this invention is to provide components which are useful in disposable products and which are degraded into less contaminating forms under the conditions typically existing in waste composting processes. These conditions may involve temperatures no higher than 70° C., averaging more nearly 55°-60° C., 100% relative humidity and exposure times which range from two weeks to more than three months.

Another object of this invention is to provide disposable components which will not only degrade aerobically in composting, but will continue to degrade in the soil or landfill anaerobically. As long as water is present, they will continue to break down into molecular weight fragments which can be ultimately biodegraded by anaerobic microorganisms completely into biogas, biomass and liquid leachate, as for natural organics like wood.

Other objects of the invention include the provision of novel polyesters for making the aforementioned fibers, films, coatings and nonwoven sheets of the polyesters, and disposable diapers containing the nonwoven sheets.

Still other objects of the invention are to provide polyesters and derivative products which have low ingredient costs and yet provide strength and toughness properties adequate for end uses such as in disposable diapers.

DESCRIPTION OF RELATED ART

Various polyester compositions have been suggested in the past for biodegradable end uses. These include polyhydroxybutyrate, polylactide, polycaprolactone, polyglycolide, and their copolymers. They have not been widely adopted in high volume uses, however, because they are either too expensive or their properties are inadequate for the uses mentioned above.

It is also known to use the salts of 5-sulfoisophthalic acid and its esters as comonomers to improve acid dyeability of polyethylene terephthalate fibers, see for example U.S. Pat. No. 3,018,272 (Griffing et al). Moreover, this type of fiber is known to have an increased rate of hydrolytic degradation, see for example J. Appl. Poly. Sci., vol 26, 4087-4094 (W. Ingamells et al.). The use of 5-sulfoisophthalate salts together with other neutral comonomers has been disclosed to increase dye rates, but the proportion of the neutral comonomer is usually minimized to affect physical properties as little as possible, see for example U.S. Pat. Nos. 4,704,329 (Hancock et al.) and 3,853,820 (Vachon).

It is also known to use as much as 20 to 45 mole % diethylene glycol as a comonomer with ethylene glycol and terephthalic to provide polyesters having suitable melting and bonding characteristics for a nonwoven binder fiber, see for example U.S. Pat. No. 4,418,116 (Scott). Further, it is known to prepare water dispersible papermaking binder fibers which are made containing to 20 mole % of diethylene glycol and preferably more than 3 mole % 5-sulfoisophthalate, see for example U.S. Pat. No. 4,483,976 (Yamamoto et al.). In the latter patent each of the specific polymers disclosed contain 7 mole % or more of the 5-sulfoisophthalate salt.

SUMMARY OF THE INVENTION

In one embodiment of the invention there is provided a novel fiber and film forming polyester consisting essentially of recurring structural units of the formula

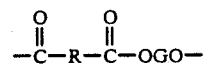

wherein R is
about 97 to 99.9 mole % para-phenylene and
about 0.1 to 3 mole % of the sulfonate radical

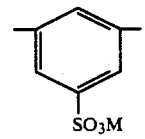

where M is an alkali metal or alkaline earth metal, and
wherein G is
about 60 to 80 mole % —CH$_2$—CH$_2$— and
about 20 to 40 mole % —(CH$_2$)$_2$—O—(CH$_2$)$_2$—.

Other embodiments of the invention include fibers, films and coatings of the above polyesters and nonwovens of the fibers. The invention also contemplates disposable products such as diapers which contain an absorbent body portion having on at least one surface thereof a water permeable nonwoven sheet composed of the polyester fibers and/or a water impermeable film of the polyester.

It is a finding of the invention that the above polyesters derived from terephthalic acid (abbreviation T), a metal salt of a 5-sulfoisophthalic acid (abbreviation MSO$_3$-I), ethylene glycol (abbreviation 2G) and diethylene glycol (abbreviation DEG) undergo degradation when subjected to the conditions of high humidity and temperature that typically characterize composting operations. It is also significant that the bulk of the monomers resulting from degradation, i.e. terephthalic acid and the glycols, are readily digested by organisms in solid waste or compost to create carbon dioxide and water.

A preferred polyester of the invention is that indicated by the abbreviation 20 DEG/80 2G//2.4 MSO$_3$-I/97.6T, where the numbers connote the mole percentages of the various glycol and diacid monomeric units in the polyester. Such abbreviations to connote compositions on a mole % basis will be used throughout this specification.

DETAILED DESCRIPTION OF PREFERRED EMBODIMENTS

The polyesters of the invention consist essentially of recurring structural units of the formula

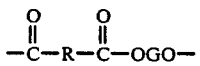

wherein R is
about 97 to 99.9 mole % para-phenylene and
about 0.1 to 3 mole % of the sulfonate radical

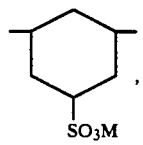

where M is an alkali metal or alkaline earth metal, and
wherein G is
about 60 to 80 mole % —CH$_2$—CH$_2$— and
about 20 to 40 mole % —(CH$_2$)$_2$—O—(CH$_2$)$_2$—.

The polyesters of the invention are water-insoluble, unlike other polyesters which might be derived from the same constituents but which contain very much higher mole percentages of MSO$_3$-I. They also have relatively low glass transition temperatures, Tg.

Thus advantageously the Tg of the polyester fibers or films should be no higher than approximately the temperature at which degradation will take place. Since the temperatures in composting operations are often no higher than about 70° C., it is desired that the Tg of the polyester be no more than about 70° C., preferably be about 65° C. or below. Commercial unmodified polyethylene terephthalate (abreviation 2GT) polyester fibers have a Tg of about 80° C. Even 2GT polyesters containing 2.5 mole % of MSO$_3$-I or 20 mole % DEG have Tg values of 76° C. and 68° C., respectively.

It will be understood that with minor variations in composition, it is possible for the polyesters of the invention to have a further significant reduction in their Tg values. For example, the replacement of up to 5 mole % of the terephthalic acid with an aliphatic acid such as azelaic, succinic, adipic, sebacic or glutaric acid or the replacement of up to 5 mole % of the ethylene glycol with another glycol such as triethylene glycol can lower the Tg even below 65° C. Such amounts will not otherwise materially alter the performance or degradation characteristics of the polyesters, hence their inclusion is contemplated by the term "consisting essentially" used to describe the polyesters and other products of the invention.

The polyesters of the invention may be prepared by conventional polycondensation techniques using, as the glycol component, a combination of about 60 to 80 mole % of ethylene glycol with complementally about 20 to 40 mole % of diethylene glycol, and as the acid component, a combination of about 97 to 99.9 mole % of terephthalic acid with about 0.1 to 3 mole % of a metal salt of 5-sulfoisophthalic acid. Optionally up to about 5 mole % of the ethylene glycol or terephthalic acid can be replaced, respectively, by another glycol or by an aliphatic acid. In lieu of the mentioned dicarboxylic acids, ester forming derivatives such as the dimethyl esters of the acids may be used.

The glycol component is preferably about 20 to 25 mole % DEG and about 75-80 mole % 2G to achieve an optimum level of degradability without a major sacrifice to fiber and film physical properties such as tensile strength. Above about 40 mole % DEG such properties are adversely affected while with less than about 20 mole % DEG, the degradability may become inadequate.

The acid component is preferably about 1.5 to 2.5 mole % MSO$_3$-I. This component is not only relatively costly but also excessively large amounts can render the polyesters water soluble and thus affect the fiber and film physical properties such as shrinkage. As little as 0.1 mole % of the MSO$_3$-I contributes significantly to the degradability characteristics of the resultant fibers and films.

In the MSO$_3$-I monomeric units, the metal ion is preferably an alkali metal such as sodium, potassium or lithium. However, alkaline earth metals such as magnesium are also useful. A preferred 5-isophthalate is the sodium salt, represented by NaSO$_3$-I.

A relative viscosity of at least 16, preferably at least about 18, is generally acceptable for melt spinning peformance.

In the Examples which follow, the various monomeric components are charged to a polymerization vessel along with an antimony or other catalyst and subjected to polycondensation conditions to produce a linear polyester in which the units are randomly distributed along the molecular chain. It will be understood that it is also possible, however, to first react two or more of the monomeric components to a prepolymer stage followed by addition of the remaining components and completion of the polymerization.

If it is desired for environmental reasons to use a catalyst that is free of antimony or other heavy metals, then there may be used a crystalline sodium aluminosilicate molecular sieve such as Linde Molecular Sieve 13X, type 9356, with a nominal pore size of 10 A, obtained from Union Carbide Corporation. This is more fully described in commonly assigned U.S. application Ser. No. 07/497,069 filed Mar. 20, 1990 in the name of Jackson.

In any event, the particular mole percentages of the aforementioned components are desirably selected to provide a polyester which in fiber or film form has a Tg of 70° C. or less, preferably of about 65° C. or less.

It will be understood that while the polyesters of the invention are well suited for use as fibers or filaments in nonwoven sheets, they can also be used to advantage in the form of cast and blown films, coatings, or molded articles wherever polyesters with such properties are desired.

An important aspect of the invention is, however, the production of fibers or filaments from the above-described polyesters. Fibers and filaments herein are interchangeable terms in the general sense, but where a more specific acknowledgement of length is appropriate, the term "fibers" is intended to refer to short filaments as in "staple fibers". Hereafter only one of the terms may be used.

The polyesters of the invention may be converted to fibers or filaments by conventional melt spinning techniques. Deniers of 2 to 15 dpf are most common. The filaments may be used as-spun (undrawn) or in a stretched (drawn or oriented) condition. Drawing to reduce denier or for increasing orientation can be accomplished by the usual procedures.

The polymer compositions of the invention can be formed into nonwoven fabrics via a number of processes. These may be roughly divided into spunbonded fabrics and those fabrics using staple fibers. These are discussed in "Encyclopedia of Textiles, Fibers and Nonwoven Fabrics", Ed. Martin Grayson, John Wiley and Sons, New York, 1984, pp 252-304. The compositions described herein can be used in many such products. Spunbonded nonwovens can be prepared by spinning and laying down simultaneously into webs, continuous filaments using known methods of distributing the threadline in the desired orientation in the web plane. Such webs can be thermally bonded under suitable conditions of time, temperature and pressure to strong fabrics with tensile properties which are usually superior to those obtained with staple webs. Bonding can also be carried out by using suitable adhesives and both these methods may be used to make point bonded or area bonded fabrics. Needle punching may also be used to give the webs stability and strength. Spunbonded fabrics can also be made by melt blowing wherein a stream of molten polymer is extruded into a high velocity stream of heated air and a bonded web formed directly on a screen conveyor from the resultant fibers. Nonwoven fabrics can also be made by direct extrusion through a rotating die into a netlike product (J. J. Smith U.S. Pat. No. 3,959,057) or by stretching and drawing embossed films of the thermoplastic polymers (British Patent 914,489 and 1,548,865 to Smith and Nephew Research Ltd.)

Staple fibers can be made into nonwovens by several processes. Most of these can be classified into (1) web preparation and (2) reinforcing ("Manual of Nonwovens" Dr. Radko Krcma, Textile Trade Press, Manchester, England, pp 74-76, 1971). During web preparation, bales of staple fiber are opened and formed into a web having either a random orientation (via air, water or electrostatic deposition) or parallel or crosslaid orientation (via carding and plying). Reinforcement to impart physical integrity and useful mechanical properties, can be accomplished by mechanical means such as needlepunching or hydroentanglement (where water jets move fibers out of the plane of the web and entangle them as in the spunlaced fabrics (Du Pont U.S. Pat. No. 3,485,706) or by stitchbonding where a reinforcing thread is sewn through the web. (See "Principles of Stitch Through Technology" Nonwovens Fabrics Forum, Clemson University Clemson, S.C. 1978 by J. D. Singelyn). Reinforcement can also be accomplished by adhesive bonding which includes impregnation of the web by a water based resin binder solution or dispersion and subsequent evaporation of the water leaving a fabric which is composed typically of 70% by weight fiber and 30% by weight binder. Dry adhesive powders may also be applied to the staple web prior to a heating step to produce a powder-bonded nonwoven. Webs of thermoplastic staple fibers may also be reinforced by thermal bonding in which use is made of the ability of the fibers to soften and adhere to each other upon application of heat. As with the spunbonded fabrics these may be point bonded or area bonded. Heat may be applied by hot air (known as through air bonding) or by a pair of patterned and/or flat heated rollers which form a nip through which the web passes to achieve bonding. This process may be carried out with 100% thermoplastic fibers or with blends of thermoplastic fibers with fibers which do not thermally bond in the 100% form, i.e. cotton and rayon.

In addition, nonwoven fabrics can also be made by laminating, extrusion melt coating or adhesively combining the above types of nonwoven fabrics with each other, with films or staple webs in such a way as to confer desired properties on the combined fabric.

In particular, a fabric made by extrusion melt coating a thin, pinhole free film of the compositions of this invention on a nonwoven, made by the spunbonded process or by thermally bonding staple from fibers of this invention alone or in combination with other compostable fibers such as cotton or rayon, is aesthetically pleasing and non-fluid permeable.

The compostable polyester fibers described herein may be used in all these methods of preparing non wovens to yield fabrics which when subjected to composting conditions will be substantially degraded. Thus staple webs of the polyester fibers described in Example 2, as well as blends of these fibers with cotton and rayon may be bonded by hydroentanglement, by needle punching, by wet resin bonding and by dry adhesive bonding. (The adhesives used should be chosen which allow the desired degradation under composting conditions.)

Thermally bonded staple webs of the described compostable polyester fibers can be made in the 100% form or webs containing a significant proportion of these fibers together with cotton and/or rayon may be thermally bonded to fabrics having useful mechanical properties as described in Example 2.

Continuous or spun yarns prepared from the compositions described herein may be used to stitch bond webs of fibers such as cotton, rayon or blends of these fibers with the compostable polyester fibers of this invention resulting in fabrics which will degrade under composting conditions.

Spunbonded fabrics can be made by thermally bonding webs of continuous fibers prepared from the compostable polyester compositions described herein and by blow spinning, direct extrusion to nets and drawing of embossed films.

The compostable compositions described herein can be melt extruded as films to coat spunlaced nonwoven fabrics which themselves may be composed of compostable fibers alone or in combination with wood pulp, rayon or cotton.

Nonwoven webs of the compostable compositions made by the melt blowing process may also be used as an adhesive layer between other nonwoven fabrics.

It is apparent that the fiber, film, and sheet products made from compositions described herein have a great number of applications in products which are disposed of or potentially may be disposed of in composting systems. In addition the compositions have utility in objects made by injection molding, injection blow molding, thermal forming of sheets, rotational molding of powder, extrusion, and pultrusion, which desirably can be disposed of and degraded in composting systems. The following is a non exclusive list of such end uses:

Agricultural mulch
Agricultural mats containing seeds, nutrients
Adhesive tape substrate
Baby pants
Bags
Bag closures
Bed sheets
Bottles
Cartons
Disposable diapers
Dust bags
Fabric softener sheets
Garment bags
Garbage and lawn waste bags
Industrial bags
Labels, tags
Packaging films and structures
Pillow cases
Protective clothing
Surgical drapes
Surgical gowns
Surgical sheets
Surgical sponges
Tampon applicators
Temporary enclosures
Temporary siding
Toys
Wipers The fibers, films and nonwoven fabrics prepared from the compositions of the present invention are of particular utility in disposable diapers since in that use they have an enhanced capability of being degraded in a composting operation. Typical examples of disposable diaper constructions are given in U.S. Pat. Nos. 3,860,003 (Buell) and 4,687,477 (Suzuki et al.), the disclosures of which are incorporated herein by reference. The items which can be made of the compostable compositions of this invention are (1) the backsheet film, i.e. the water-impermeable outside layer, which may be a film which is 100% of the compostable composition or it may be a laminated sheet with a nonwoven or web of compostable fibers including cotton or rayon adhered to the film, (2) the topsheet, i.e. the water-permeable or inner layer, which is a nonwoven fabric of the compostable fiber composition or a blend of the compostable fiber of this invention with cotton or rayon fiber having a porosity suitable for passing urine quickly to the fluid-absorbing pad between the topsheet and backsheet film, and (3) the fastening tapes which may optionally be made from films or nonwovens of the compositions of the invention. The fastening tapes are typically coated with a pressure sensitive adhesive.

It will be apparent that the products of the invention may contain additives such as dyes, pigments, fillers, etc.

In the Examples which follow:

Polyester glass transition temperatures, $T_g$, are obtained by using a Du Pont model 2910 Differential Scanning Calorimeter. Samples are heated under a nitrogen atmosphere at a rate of 20° C./min. to a temperature 10°–20° C. above the melting point, then the melt is cooled using the rapid air quench capability of the instrument. The $T_g$ is determined from the second cycle scan done at 20° C./min. using the internal software to determine the inflection point of the baseline shift.

Polymer melting point, m.p., is determined on the first heating cycle as described in Tg determination. The temperature at which the maximum of the endothermic peak which occurs at the highest temperature is reported as the polymer melting point.

Number average molecular weight, $M_n$, is determined by gel permeation chromatography (gpc) versus a standard polyethylene terephthalate sample with an Mn of 22000 and a weight average molecular weight of 44000. Polymers are dissolved in and the analysis is run using HFIP containing 0.01M sodium trifluoroacetate as the solvent. A Waters model 150C ALC/GPC instrument, or its equivalent, is used with two Zorbax PSM-S biomodal columns (sold by E. I. du Pont de Nemours and Company) (or equivalent) in series at 30° C. A refractive index detector was used and data collected at 100 intervals and analyzed via software provided by the instrument supplier.

Carboxyl end groups are determined by titration of an o-cresol solution of the polymer at 115° C. with KOH in benzyl alcohol to a colorimetric endpoint using bromophenol blue as the indicator. Results are reported in eq./$10^6$ grams of polymer.

Inherent viscosity is defined in "Preparative Methods of Polymer Chemistry", W. R. Sorenson and T. W. Campbell, 1961, p. 35. It is determined at a concentration of 0.5 g/100 ml of the indicated solvent at the indicated temperature.

Relative viscosity is the ratio of the viscosity of a solution of 0.8 grams of polyester dissolved in 10 ml of hexafluoroisopropanol (HFIP) containing 80 ppm $H_2SO_4$ to the viscosity of $H_2SO_4$-containing HFIP itself, both measured at 25° C. in a capillary viscometer and expressed in the same units.

Crimp index is measured by straightening a crimped tow by application of about 0.1 gpd load. Then 0.5 gm clips 66.6 cm apart are attached to the extended tow. The tow is then cut 11.2 cm beyond each clip to give a sample of 90 cm extended length. The sample is suspended vertically, hanging freely from one of the clips to allow retraction to crimped length. After about 30 secs., clip-to-clip distance is measured.

$$\text{Crimp Index} = \frac{(66.6 - Lc)}{66.6} \times 100$$

where Lc is the clip-to-clip distance in the free-hanging state.

Crystallinity index is measured by first obtaining a diffractogram as described by Blades (U.S. Pat. No. 3,869,429, col. 12) with some modifications. The high intensity X-ray source is a Phillips XRG-3100 with a long fine focus copper tube. Diffraction is analyzed with a Phillips single axis goniometer equipped with a theta-compensating slit and a quartz monochromator set to exclude copper $K_\beta$ radiation. Diffracted radiation is collected in step scanning mode in 0.025° steps with a 1.5 sec. per step count time. The digital data so collected are analyzed by a computer and smoothed by a running fit to second order polynomial. The computer is programmed to define a straight base line which joins the diffractogram tangentially at about 11° and 34°. Crystallinity index is defined as $$\frac{A \times 100}{A - B}$$

where A is the intensity of the 18° 010 peak above this base line and B is the intensity of the 20° minimum above this base line. Crystallinity index has been related to percent crystallinity determined by density (see U.S. Pat. No. 4,704,329, col. 8, 9) Weight percent crystallinity = 0.676 × Crystallinity index.

The invention will be further illustrated by the following examples wherein parts and percentages are by weight unless otherwise indicated.

EXAMPLE 1

This example illustrates the laboratory preparation of a copolyester of the invention, the spinning of fibers thereof, and the testing of the fibers for an indication of degradability, i.e. measuring hydrolysis upon exposure to hot water. The copolyester is prepared to contain 20 mole % DEG/80 mole % 2G//2.4 mole % $NaSO_3$-I/97.6 mole % T. Some small deviation in glycol content may result as some DEG may be distilled off during the polymerization.

In a one liter 3-necked flask fitted with a stirrer, $N_2$ inlet and distillation head are placed:
334.8 g ethylene glycol
0.407 g $Mn(OAc)_2.4H_2O$
0.218 g $Sb_2O_3$
0.278 g NaOAc.

This is heated to 160° C. in an oil bath until all components are dissolved. Then there is added:
63.6 g diethylene glycol
564.9 dimethyl terephthalate
21 06 g $NaSO_3$-I dimethylester.

The temperature of the oil bath is slowly increased. Distillate (methanol) in the amount of 232 ml is collected between 180°-220° C. Then 2 ml of a $H_3PO_4$ solution in ethylene glycol is added (4.79 g 85% $H_3PO_4$ diluted to 50 ml with ethylene glycol) and the mixture is stirred for 5 min. The resultant molten monomer is then used to fill a polymer tube about two-thirds full.

Polymerization is continued by attaching a filter flask to the side arm of the polymer tube and inserting a capillary inlet tube drawn finely which reaches to the bottom of the molten monomer pool. Nitrogen gas is bled in as the tubes are heated in a dimethyl phthalate vapor bath (284° C.), first under laboratory vacuum for 1 hour, then at 0.3 mm Hg using a vacuum pump for 5 hours.

The capillary tube is removed from the molten polymer and the polymer is allowed to cool. The polymer is recovered and ground into small particles in a Thomas mill. The resulting flake is dried at about 130° C. overnight under laboratory vacuum. The inherent viscosity of the flake is 0.71 (HFIP at 25° C.).

Yarn is melt spun twice at different temperatures, delivery and windup speeds, through a 5 hole spinneret with 0.015 inch diameter × 0.045 inch length orifices directly onto a windup. No finish is applied to the yarns.

The 5 filament yarns are each skeined into 20 ply yarns, then are drawn in segments over a hot pin to yield two yarns identified as A and B, as shown in Table I. The Tg of B is 68° C. and the polymer MP is 211° C.

A third yarn, identified as Control, is made by the same polymerization, spinning and drawing steps except that no $NaSO_3$-I is used and minor changes are made in the spinning and drawing. Thus, the acid component of the Control is 100 mole % terephthalic acid.

Hydrolysis testing of all three yarns is carried out by enclosing each yarn strand (about 40 filaments about 20 cm. long) in a cheesecloth bag, then boiling the sample for eight hours in distilled water.

While the tenacity loss data is not highly reproducible on this laboratory scale, it is clear that those yarns prepared according to the invention are much more susceptible to hydrolysis, hence will degrade more rapidly, than the Control sample prepared without $NaSO_3$-I.

TABLE I

| Sample | Mole % $NaSO_3$-I | Spin. Temp., °C. | Del. Speed. cc/min. | Windup Speed m/min. | Draw Ratio Temp. °C. | % Tenacity Loss |
|---|---|---|---|---|---|---|
| A | 2.4 | 218° | 2.8 | 250 | 1.4X/60° | 65 |
| B | 2.4 | 223° | .7 | 250 | 1.5X/60° | 75 |
| Control | 0 | 230° | 1.3 | 335 | 3.7X/70° | 20 |

The above samples are exposed to a laboratory aerobic composting reactor which is run in a controlled manner to provide a uniform environment. Short lengths of the yarns are interwoven between the apertures of a polypropylene mesh fabric to ensure even exposure of the yarn, and these specimens are placed in the laboratory reactor. The reactor contains an innoculum from a municipal composting plant which, after removal of non-organics, has gone through intensive aeration during 2-3 days of composting and to which water has been added to a moisture content of 50%. The reactor is allowed to increase in temperature from 30° to 50° C. in over two days while dry air is passed through the reactor at a rate sufficient for the aerobic bacterial to thrive. The mixture is maintained at 50° C. by controlling the temperature of a surrounding water bath for an additional 10 days. The reduction in tensile strength measured for recovered Sample A is 70% and for Sample B 40%. The reduction in tensile strength of the Control is 5%.

EXAMPLE 2

This example demonstrates the preparation of a compostable polyester of the invention from ingredients which include diethylene glycol, ethylene glycol, sodium dimethyl isophthalate-5-sulfonate and dimethyl terephthalate. The copolyester so prepared is found by chemical analysis to contain 25 mole % DEG/75 mole % 2G//2 mole % $NaSO_3$-I/98 mole % T.

There is used for the polymerization a conventional four-vessel continuous polymerization system for polyesters coupled to a spinning machine. Diethylene glycol and sodium dimethyl isophthalate-5-sulfonate are added to a mix tank containing ethylene glycol and catalysts. The catalyst is a mixture of manganese acetate, antimony trioxide, and sodium acetate in the ratios of 5.0/5.6/1, respectively. The entire mixture is continuously fed from the mix tank to the first vessel where the ester interchange reaction is carried out. The temperatures in this vessel ranges from approximately 65° C. at the top of the column to approximately 235° C. at the bottom. The vessel is operated at atmospheric pressure with a hold-up time of about 65 minutes. Dimethyl terephthalate in molten form is directly metered into the first vessel. Pure, uncatalyzed glycol is metered into the vessel to adjust the catalyst level to approximately 125 ppm Mn based on the polymer to be formed. The mole ratio of total glycols (ethylene glycol and diethylene glycol) to dimethyl terephthalate/sodium dimethyl isophthalate-5-sulfonate is 2.0 to 1.

To the liquid monomer product of the ester interchange vessel is added sufficient phosphoric acid to give approximately 95 ppm phosphorus based upon polymer and a sufficient amount of a slurry of 5 percent TiO2 in ethylene glycol to give approximately 0.3 percent of the delusterant in the polymer. The mixture is then transferred to the second vessel where the temperature is increased to about 245° C. and the pressure is reduced to about 100 mm mercury as polymerization is initiated for about 26 minutes in the conventional manner. Excess glycol is removed through a vacuum system.

The low molecular weight material is then pumped to a third vessel where the temperature is increased to about 270° C. and the pressure is reduced to about 30 mm mercury. Excess glycol is again removed through a vacuum system over a period of about 12 minutes.

The low molecular weight polymer so obtained is then transferred to a fourth vessel where the temperature is controlled at 275° C. and the pressure is reduced to 3-7 mm mercury. The pressure is automatically adjusted to maintain the polymer melt viscosity, as determined by an in-line viscometer. After about 200 minutes, the polymer is recovered and found to have a relative viscosity (RV) of approximately 16. Upon analysis for DEG by gas chromatography and for 5-SO$_3$Na-I by x-ray fluorescence, the polymer composition is determined to have the composition described above.

The polymer is then spun into monocomponent filaments by extruding through orifices (of about 0.38 mm diameter) of a spinneret maintained at 275° C. As the filaments exit the spinneret, they are quenched with air at 21° C., collected into a bundle, and then about 0.2 percent of a spin finish is applied. The finish is a 3.5 percent emulsion in water of a mixture of an anionic surfactant, which is Zelek NK, available from E. I. du Pont de Nemours and Company, and a nonionic lubricant, which is Nopco 2152P, available from Henkel Corporation. The filaments are wound at 1200 yards per minute to give a yarn containing 900 filaments and a total denier of 4500.

Bundles of yarn are collected together forming a tow of approximately 36,000 filaments which are drawn in two stages. The tow is drawn in the first stage at a draw ratio of 2.8X followed by a second draw of 1.11X to give a total draw ratio of 3.1X. The fibers are crimped in a stuffer box crimper and heat-treated under essentially no restraint in an oven for 8 minutes at 120° C. At oven temperatures of 130° C., the fibers would adhere together forming a stiff, harsh fused tow. The resultant filaments coded 2A have a denier of 2.5, a tenacity of 2.5 grams/denier, a shrinkage in boiling water of 40.4 percent, a shrinkage in dry heat at 160° C. of approximately 7.0 percent, a crimp level of 11-12 crimps per inch, and a crimp index of approximately 17. The melting point of the fiber is determined to be 195° C. The same procedure is followed except that after drawing to a draw ratio of 3.1X, the fibers are heat-treated at constant length (under tension) using electrically heated rolls set at 140° C. At roll temperature settings of 150° C., the fibers would soften and adhere together and to process equipment. The fibers are then crimped in a stuffer box crimper and dried in an oven at 80° C. for 8 minutes. The resultant filaments coded 2B have a denier of 2.0, a tenacity of 3.2 grams/denier, a shrinkage in boiling water of 46.2 percent, a shrinkage in dry heat at 160° C. of approximately 18 percent, a crimp level of 12-13 crimps per inch, and a crimp index of approximately 26.

The crystallinity index of 2A is 44 and of 2B is 33. The carboxyl end group concentration of 2A is 37 eq./$10^6$ grams and of 2B is 38 eq./$10^6$ grams.

The hydrolytic stability of these fibers, as well as 2GT binder fibers containing about 24 mole % DEG and no 5-NaSO$_3$-I prepared according to U.S. Pat. No. 4,418,116, is measured by subjecting them to boiling water for 24 hours. The results are summarized in Table II.

TABLE II

|  | Tenacity Reduction (%) | Molecular Weight (Mn) Reduction (%) |
| --- | --- | --- |
| 2A | 100 | 80 |
| 2B | 100 | 83 |
| Control | — | +7%* |

*Probably due to extraction of oligomers.

Clearly the added presence of a small percentage of 5-NaSO3-I has greatly contributed to the degradability of the polymers of the invention.

Films having the same composition as the 2A fibers above are made by pressing fiber, from which the finish is first removed by washing with ethyl alcohol, in a hot press at 195° C. with a pressure of 20,000 psi. The films, having thicknesses between 2 and 7 mils, are then hydrolyzed in water at 100° C. for 24 hours. They show a reduction in molecular weight from 34400 to 10700. The slightly lower degree of molecular weight reduction versus the fiber is probably due to the thickness of films leading to nonuniform water penetration.

A portion, of the 2A fibers is cut to staple length of 1½ inches and processed into a web of about 0.7 oz./sq. yard by conventional opening and carding steps. The web is thermally bonded at a temperature of about 135°-145° C. in a hot air oven to yield a nonwoven fabric of excellent physical integrity and strength. A portion of the 2B fibers is blended 50:50 with cotton fibers and bonded at about 156° C. by the same procedure to produce a second fabric.

Both nonwovens are useful as the water permeable topsheets of a diaper construction of the type shown in U.S. Pat. No. 4,687,477. The aforementioned films made by casting or blowing are also useful as the water impermeable backsheet of such diaper constructions.

Melt extrusion of a pinhole-free film, which is less than 0.7 mil thick, of the composition in this Example onto the thermally bonded nonwoven fabrics of this Example having a basis weight of 25 oz/yd$^2$ or less gives a non-fluid permeable fabric having a softer feel, which makes it useful in applications such as a diaper backsheet.

EXAMPLE 3

This example shows the effect of producing a polymer containing 0.4 mole % 5-NaSO$_3$-I and 20 mole % DEG.

In a 350 ml resin kettle heated with a Woods metal bath, fitted with a paddle stirrer, a nitrogen inlet tube and a distillation head are placed 33.4 g of ethylene glycol, 0.041 g Mn(OAc)$_2$.4H$_2$O, 0.022 g Sb$_2$O$_3$ and 0.028 g of sodium acetate. This mixture is stirred under nitrogen and heated to 160° C. until the solids dissolve. Then 59.76 g of dimethyl terephthalate, 6.56 g diethylene glycol and 0.36 g dimethyl sodium 5-sulfoisophthalate are added and the temperature is gradually increased to 240° C. while distillate is collected. This takes about 55 min. Then 0.2 ml of a 10% solution of 85% H$_3$PO$_4$ in ethylene glycol is added and the temperature is increased to 285° C. while the vacuum is gradually increased to 0.4 mm Hg over a period of about 3.5 hours. The polymer is scooped out of the reactor while it is still hot. After cooling, the polymer is ground using a Thomas cutter to about ⅛" particles. The inherent viscosity is 0.47 (m-cresol at 30° C.). These are dried overnight in a vacuum oven at 100° C., then molded into a ⅜" diameter rod at 190° C. This rod is inserted into a hydraulically driven melt spinning apparatus. Spinning is carried out through a spinneret with 5 holes in 0.015" diameter×0.045" long at a temperature of 240° C. and a delivery speed of about 0.7 cc/min. Fiber is wound up at a speed of 261 m/min. After plying the 5 filament yarn 20 times, it is drawn 3X over a 90° C. hot pin. Analysis of the molecular weight of the fiber by gel permeation chromatography (gpc) gives a molecular weight (Mn) of 27300. Samples of fiber are placed in a large excess of distilled water and heated to reflux for 24 hours to test their stability. Samples analyzed by gpc show a reduction in Mn of 30%.

EXAMPLE 4

This example illustrates the laboratory preparation of a copolyester of the invention, the casting of film thereof, the blowing of film thereof, and the testing of the film for an indication of hydrolysis upon exposure to hot water. The copolyester is prepared to contain 20 mole % DEG/80 mole % 2G//2.0 mole % NaSO$_3$-I/98 mole % T. Some small deviation in glycol content may result as some DEG may be distilled off during the polymerization and additional DEG is produced as a byproduct of polymerization.

In a 35 gallon reactor containing a stirrer, a nitrogen inlet and a distillation column are placed:

| | |
|---|---|
| 44,946 grams | dimethylterephthalate |
| 23,608 grams | ethylene glycol |
| 5,039 grams | diethylene glycol |
| 1,475 grams | NaSO$_3$-I dimethyl ester |
| 29 grams | Mn(OAc)2.4H$_2$O |
| 17 grams | Sb$_2$O$_3$ |
| 20.4 grams | NaOAc.3H$_2$O |

The temperature of the reactor is slowly increased. Distillate (methanol) in the amount of 14,000 ml is collected between 180°-210° C. A second distillate (ethylene glycol) in the amount of 5,000 ml is collected between 210°-240° C. The resultant oligomer is transferred to a second vessel containing an agitator and vacuum capabilities. Then 20.3 ml of H$_3$PO$_4$ (85%) is added to the transferred material and maximum vacuum is slowly established over 90 minutes. During this time the reactor content temperature is increased to 276° C. The temperature is held constant at 276° C. for 2.5 hours while the vacuum slowly increases from 1.9 mm Hg to 0.6 mm Hg. The pressure in the reactor is quickly increased to 60 PSIG and the polymer is discharged through the bottom valve, formed into a ribbon, quenched in water and cut into flake. The inherent viscosity of the flake is 0.86 (HFIP, 30° C.). The flake is dried at 65° C. overnight under laboratory vacuum.

Film is formed by two processes. In the first process the dried flake is fed to a 1 inch extruder, melted and forced through a 6 inch film die with a 10 mil gap, quenched on 50° C. chill rolls and collected on a windup roll. The speed of the extruder and quench system are adjusted in combination with the temperature of the extruder and quench system to form cast film between 1 and 20 mils thick. The average tensile strength, modulus and elongation of 1.9 mil thick film are 6,570 psi, 253,000 psi and 2.9%.

In the second process the dried flake is fed to a ¾ inch extruder, melted and forced through a 1 inch blown film die with an adjustable gap, inflated with nitrogen and collected. The die gap, speed of the extruder and collection system are adjusted in combination with the extruder temperatures and nitrogen flow rates to form blown film. With a gap of about 5 mils, films with thicknesses between 0.25 and 5 mils are obtained. The average tensile strength, modulus and elongation of 0.43 mil thick samples are 4,900 psi, 205,000 psi and 33%. A sample of the 0.4 mil thick film disintegrates into fragments on boiling it in water for 24 hours.

What is claimed is:

1. A fiber and film forming polyester consisting essentially of recurring structural units of the formula

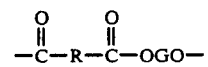

wherein R is
about 97 to 99.9 mole % para-phenylene and
about 0.1 to 3 mole % of the sulfonate radical

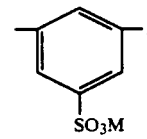

where M is an alkali metal or
alkaline earth metal, and
wherein G is
about 60 to 80 mole % —CH$_2$—CH$_2$— and
about 20 to 40 mole % —(CH$_2$)$_2$—O—(CH$_2$)$_2$—.

2. Polyester according to claim 1 wherein R is about 98 mole % para-phenylene and about 2% of the sulfonate radical, and G is about 80 mole % —CH$_2$—CH$_2$— and about 20 mole % —(CH$_2$)$_2$—O—(CH$_2$)$_2$—.

3. A fiber of the polyester of claim 1.
4. A fiber of the polyester of claim 2.
5. A non-woven sheet of the polyester of claim 1.
6. A non-woven sheet of the polyester of claim 2.
7. A film of the polyester of claim 1.
8. A film of the polyester of claim 1 applied as a coating to a layer of nonwoven sheet.

9. A disposable diaper which includes an absorbent body portion having on one surface thereof a water permeable nonwoven sheet of fibers of the polymer of claim 1.

10. A disposable diaper which includes an absorbent body portion having on one surface thereof a water impermeable film of the polymer of claim 1.

11. Polyester according to claim 1 wherein the amount of the sulfonate radical is about 1.5 to 2.5 mole %.

* * * * *